United States Patent [19]
Pitteloud et al.

[11] Patent Number: 5,616,780
[45] Date of Patent: Apr. 1, 1997

[54] BISPHENOL ESTER DERIVATIVES

[75] Inventors: Rita Pitteloud, Praroman, Switzerland; Bernard Gilg, St. Louis-la-Chaussée, France

[73] Assignee: Ciba-Geigy Corporation, Tarrytown, N.Y.

[21] Appl. No.: 594,199

[22] Filed: Jan. 31, 1996

[30] Foreign Application Priority Data

Aug. 2, 1995 [CH] Switzerland ................ 368/95

[51] Int. Cl.$^6$ .................................. C07C 261/00
[52] U.S. Cl. ................ 560/118; 252/404; 524/111; 524/285; 549/60; 549/79; 549/463; 549/484; 558/426; 560/8; 560/120
[58] Field of Search ................ 560/118, 8, 120; 549/60, 79, 463, 484; 558/426; 524/111, 285; 252/404

[56] References Cited

U.S. PATENT DOCUMENTS

| | | | |
|---|---|---|---|
| 4,365,032 | 12/1982 | Yosizato et al. | 524/99 |
| 4,414,408 | 11/1983 | Cottman | 560/144 |
| 5,128,398 | 7/1992 | Sasaki et al. | 524/291 |

FOREIGN PATENT DOCUMENTS

| | | |
|---|---|---|
| 0479560 | 4/1992 | European Pat. Off. |
| 0500323 | 8/1992 | European Pat. Off. |
| 2948969 | 6/1980 | Germany. |
| 3718751 | 1/1988 | Germany. |
| 4308581 | 10/1992 | Japan. |

OTHER PUBLICATIONS

Derwent Abstract 88–008082/02 of DE 3,718,751 (1988).
J.A.C.S., Louis E. Friedrich et al., vol. 94, p. 1193, (1972).
H. Kotsuki et al., Bull. Chem. Soc. Jpn., vol. 57, pp. 3339–3340 (1984).
A.F. Jacobine et al., Journal of Applied Polymer Science, vol. 45, pp. 471–485 (1992).
Ronald R. Sauers et al., J. Org. Chem., vol. 38, No. 4, pp. 642–646 (1973).
UIF Pindur et al., Chem. Rev., vol. 93, pp. 741–761 (1993).
Comprehensive Organic Synthesis, vol. IV, pp. 314–316 (1991), Pergamon Press.

Primary Examiner—Michael L. Shippen
Attorney, Agent, or Firm—Michele A. Kovaleski

[57] ABSTRACT

The novel compounds of the formula I

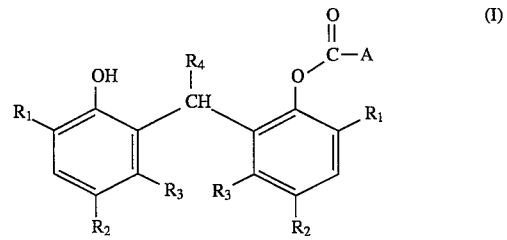

in which A is a group of the formula IIa or IIb,

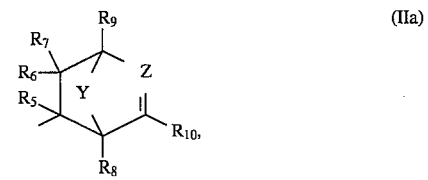

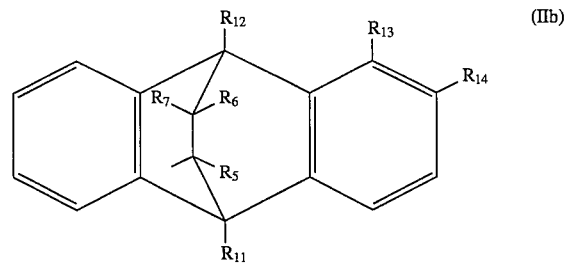

Y is oxygen, methylene, ethylidene or a $>C=C(CH_3)_2$ group, Z is nitrogen,

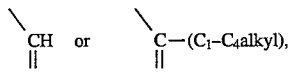

$R_1$ and $R_2$ are, for example $C_1$–$C_5$alkyl, $R_3$ and $R_4$ are, for example, hydrogen or methyl, and $R_5$, $R_6$, $R_7$, $R_8$, $R_9$, $R_{10}$, $R_{11}$, $R_{12}$, $R_{13}$ and $R_{14}$ are, for example, hydrogen, are suitable for stabilizing organic material against oxidative, thermal or light-induced degradation.

14 Claims, No Drawings

BISPHENOL ESTER DERIVATIVES

The present invention relates to novel bisphenol ester derivatives, to their use, and to organic material stabilized against oxidative, thermal and light-induced degradation with the aid of these compounds.

The use of some bisphenol ester derivatives as stabilizers is described, for example, in JP-A-Hei 4-308 581, DE-A-3 718 751, EP-A-479 560 and U.S. Pat. No. 4,414,408.

The present invention relates to a compound of the formula I

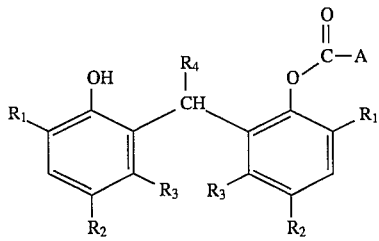

in which
A is a group of the formula IIa or IIb,

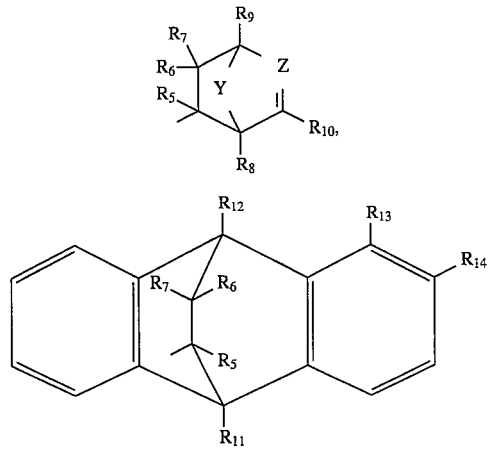

Y is oxygen, methylene, ethylidene or a >C=C(CH$_3$)$_2$ group,
Z is nitrogen,

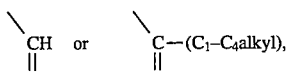

the radicals $R_1$, independently of one another, are $C_1$–$C_{25}$alkyl, $C_2$–$C_{24}$alkenyl, $C_5$–$C_{12}$cycloalkyl, $C_1$–$C_4$alkyl-substituted $C_5$–$C_{12}$ cycloalkyl, $C_5$–$C_{12}$cycloalkenyl, $C_1$–$C_4$alkyl-substituted $C_5$–$C_{12}$cycloalkenyl, phenyl, $C_1$–$C_4$alkyl-substituted phenyl, $C_7$–$C_9$phenylalkyl or —CH$_2$—S—X$_1$, the radicals $R_2$, independently of one another, are hydrogen, $C_1$–$C_{25}$alkyl, $C_2$–$C_{24}$alkenyl, $C_5$–$C_{12}$cycloalkyl, $C_1$–$C_4$alkyl-substituted $C_5$–$C_{12}$cycloalkyl, $C_5$–$C_{12}$cycloalkenyl, $C_1$–$C_4$alkyl-substituted $C_5$–$C_{12}$cycloalkenyl, phenyl, $C_1$–$C_4$alkyl-substituted phenyl, $C_7$–$C_9$phenylalkyl, —CH$_2$—S—X$_1$, —(CH$_2$)$_p$COO—X$_2$ or —(CH$_2$)$_q$O—X$_3$,
the radicals $R_3$, independently of one another, are hydrogen or $C_1$–$C_4$alkyl,
$R_4$ is hydrogen or $C_1$–$C_8$alkyl,
$R_5$ is hydrogen, $C_1$–$C_{10}$alkyl, phenyl, —CH$_2$—COO—X$_4$ or CN,
$R_6$ is hydrogen, $C_1$–$C_4$alkyl, phenyl, —COO—X$_5$, —CN or —CON(X$_6$)(X$_7$), $R_7$ is hydrogen or $C_1$–$C_{10}$alkyl,
$R_8$, $R_9$ and $R_{10}$, independently of one another, are hydrogen or $C_1$–$C_4$alkyl,
$R_{11}$ and $R_{12}$, independently of one another, are hydrogen, $C_1$–$C_4$alkyl or phenyl,
$R_{13}$ and $R_{14}$, independently of one another, are hydrogen or $C_1$–$C_4$alkyl,
$X_1$ is $C_1$–$C_{25}$alkyl, $C_5$–$C_{12}$cycloalkyl, $C_1$C$_4$alkyl-substituted $C_5$–$C_{12}$cycloalkyl, phenyl, $C_1$–$C_4$alkyl-substituted phenyl, $C_7$–$C_9$phenylalkyl or —(CH$_2$),COO—Y$_1$,
$X_2$, $X_4$ and $X_5$, independently of one another, are $C_1$–$C_{25}$alkyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl or $C_7$–$C_9$phenylalkyl,
$X_3$ is $C_1$–$C_{25}$alkyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl, $C_7$–$C_9$phenylalkyl, $C_3$–$C_{25}$alkanoyl, $C_3$–$C_{25}$alkenoyl, $C_3$–$C_{25}$alkanoyl which is interrupted by oxygen, sulfur or >N—Y$_2$, $C_6$–$C_9$cycloalkylcarbonyl, benzoyl, $C_1$–$C_4$alkyl-substituted benzoyl, thenoyl or furoyl,
$X_6$ and $X_7$, independently of one another, are hydrogen, $C_1$–$C_{25}$alkyl, $C_2$–$C_{24}$alkenyl, $C_5$–$C_{12}$cycloalkyl, $C_1$–$C_4$alkyl-substituted $C_5$–$C_{12}$cycloalkyl, $C_5$–$C_{12}$cycloalkenyl, $C_1$–$C_4$alkyl-substituted $C_5$–$C_{12}$cycloalkenyl, phenyl, $C_1$–$C_4$alkyl-substituted phenyl or $C_7$–$C_9$phenylalkyl,
$Y_1$ is $C_1$–$C_{25}$alkyl, $C_5$–$C_{12}$cycloalkyl, $C_1$–$C_4$alkyl-substituted $C_5$–$C_{12}$cycloalkyl, phenyl, $C_1$–$C_4$alkyl-substituted phenyl or $C_7$–$C_9$phenylalkyl,
$Y_2$ is hydrogen or $C_1$–$C_8$alkyl,
p is 0, 1 or 2,
q is an integer from 0 to 8, and
r is 1 or 2.

Alkyl having up to 25 carbon atoms, preferably having up to 18 carbon atoms, in particular having up to 10 carbon atoms, is, for example, methyl, ethyl, propyl, isopropyl, n-butyl, sec-butyl, isobutyl, tert-butyl, 2-ethylbutyl, n-pentyl, tert-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl.

One of the preferred meanings of $R_1$ and $R_2$ is branched alkyl having up to 10 carbon atoms, in particular having up to 5 carbon atoms, for example tert-butyl or tert-pentyl.

One of the preferred meanings of $R_4$ is $C_1$–$C_4$alkyl, in particular methyl.

One of the preferred meanings of $Y_2$ is $C_1$–$C_4$alkyl, in particular methyl.

Alkenyl having up to 24 carbon atoms, in particular having up to 18 carbon atoms, is, for example, vinyl, propenyl, isopropenyl, 2-butenyl, 3-butenyl, isobutenyl, 3-methyl-but-2-enyl, n-oct-2-enyl, n-dodec-2-enyl, isododecenyl, n-octadec-2-enyl or n-octadec-4-enyl. Alkenyl radicals in which the carbon atom in the 1-position is saturated are preferred. $C_3$–$C_{18}$Alkenyl is particularly preferred.

Unsubstituted or $C_1$–$C_4$alkyl-substituted $C_5$–$C_{12}$cycloalkyl is, for example, cyclopentyl, cyclohexyl, cycloheptyl, cyclooctyl, cyclododecyl, 2- or 4-methylcyclohexyl, dimethylcyclohexyl, trimethylcyclohexyl or tert-butylcyclohexyl. Unsubstituted or $C_1$–$C_4$alkyl-substituted $C_5$–$C_8$cycloalkyl, in particular cyclohexyl, is preferred.

Examples of unsubstituted or $C_1$–$C_4$alkyl-substituted $C_5$–$C_{12}$cycloalkenyl, preferably $C_5$–$C_8$cycloalkenyl, are cyclohex-2-enyl, cyclohept-3-enyl and 4-tert-butylcyclohex-2-enyl. Cyclohexenyl is preferred.

$C_1$–$C_4$alkyl-substituted phenyl is, for example, methylphenyl, dimethylphenyl, trimethylphenyl, ethylphenyl, diethylphenyl, isopropylphenyl, tert-butylphenyl, di-tert-butylphenyl or methyl-di-t-butylphenyl.

Examples of $C_7$–$C_9$phenylalkyl which is unsubstituted or substituted on the phenyl ring by $C_1$–$C_4$alkyl, are benzyl, phenethyl, 3-phenylpropyl, α-methylbenzyl, α,α-dimethylbenzyl, methylbenzyl, dimethylbenzyl, trimethylbenzyl and tert-butylbenzyl.

Alkanoyl having up to 25 carbon atoms is, for example, methanoyl, ethanoyl, propanoyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, octadecanoyl, nonadecanoyl or eicosanoyl. $C_1$–$C_{18}$alkanoyl is preferred.

Examples of $C_3$–$C_{25}$alkanoyl which is interrupted by oxygen, sulfur or >N—$Y_2$ are —CO—$CH_2CH_2$—S—($C_1$–$C_{10}$alkyl), —CO—$CH_2CH_2$—O—($C_1$–$C_{10}$alkyl) and —CO—$CH_2CH_2$—N($Y_2$)—($C_1$–$C_{10}$alkyl). $C_3$–$C_{25}$Alkanoyl which is interrupted by oxygen or >N—$Y_2$ is preferred.

Examples of $C_3$–$C_{25}$alkenoyl are acryloyl, methacryloyl, crotonoyl, isocrotonoyl and oleoyl. $C_3$–$C_{18}$Alkenoyl is preferred.

$C_6$–$C_9$cycloalkylcarbonyl is, for example, cyclopentylcarbonyl, cyclohexylcarbonyl, cycloheptylcarbonyl or cyclooctylcarbonyl.

$C_1$–$C_4$alkyl-substituted benzoyl is, for example, methylbenzoyl or tert-butylbenzoyl.

Preference is given to a compound of the formula I in which the radicals $R_1$, independently of one another, are $C_1$–$C_{18}$alkyl, $C_2$–$C_{18}$alkenyl, $C_5$–$C_8$cycloalkyl, $C_1$–$C_4$alkyl-substituted $C_5$–$C_8$cycloalkyl, $C_5$–$C_8$cycloalkenyl, $C_1$–$C_4$alkyl-substituted $C_5$–$C_8$cycloalkenyl, phenyl, $C_1$–$C_4$alkyl-substituted phenyl, $C_7$–$C_9$phenylalkyl or —$CH_2$—S—$X_1$, the radicals $R_2$, independently of one another, are hydrogen, $C_1$–$C_{18}$alkyl, $C_2$–$C_{18}$alkenyl, $C_5$–$C_8$cycloalkyl, $C_1$–$C_4$alkyl-substituted $C_5$–$C_8$cycloalkyl, $C_5$–$C_8$cycloalkenyl, $C_1$–$C_4$alkyl-substituted $C_5$–$C_8$cycloalkenyl, phenyl, $C_1$–$C_4$alkyl-substituted phenyl, $C_7$–$C_9$phenylalkyl, —$CH_2$—S—$X_1$, —$(CH_2)_p$COO—$X_2$ or —$(CH_2)_q$O—$X_3$, $R_5$ is hydrogen, $C_1$–$C_{10}$alkyl, phenyl or CN, $R_6$ is hydrogen, $C_1$–$C_4$alkyl or phenyl, $X_1$ is $C_1$–$C_{18}$alkyl, $C_5$–$C_8$cycloalkyl, $C_1$–$C_4$alkyl-substituted $C_5$–$C_8$cycloalkyl, phenyl, $C_1$–$C_4$alkyl-substituted phenyl, $C_7$–$C_9$phenylalkyl or —$(CH_2)_r$COO—$Y_1$, $X_2$ is $C_1$–$C_{18}$alkyl, $C_5$–$C_8$-cycloalkyl, $C_1$–$C_4$-alkyl-substituted $C_5$–$C_8$cycloalkyl, phenyl, $C_1$–$C_4$-alkyl-substituted phenyl or $C_7$–$C_9$phenylalkyl, $X_3$ is $C_1$–$C_{18}$alkyl, $C_5$–$C_8$cycloalkyl, $C_1$–$C_4$alkyl-substituted $C_5$–$C_8$cycloalkyl, phenyl, $C_1$–$C_4$alkyl-substituted phenyl, $C_7$–$C_9$phenylalkyl, $C_1$–$C_{18}$alkanoyl, $C_3$–$C_{18}$alkenoyl, $C_3$–$C_{18}$alkanoyl which is interrupted by oxygen or >N—$Y_2$, $C_6$–$C_9$cycloalkylcarbonyl, benzoyl, $C_1$–$C_4$alkyl-substituted benzoyl, thenoyl or furoyl, and $Y_1$ is $C_1$–$C_{18}$alkyl, $C_5$–$C_8$cycloalkyl, $C_1$–$C_4$alkyl-substituted $C_5$–$C_8$cycloalkyl, phenyl, $C_1$–$C_4$alkyl-substituted phenyl or $C_7$–$C_9$phenylalkyl.

Preference is likewise given to compounds of the formula I in which the radicals $R_1$, independently of one another, are $C_1$–$C_{10}$alkyl, $C_2$–$C_{18}$alkenyl, $C_5$–$C_8$cycloalkyl, $C_5$–$C_8$cycloalkenyl, phenyl, $C_7$–$C_9$phenylalkyl or —$CH_2$—S—$X_1$, the radicals $R_2$, independently of one another, are hydrogen, $C_1$–$C_{10}$alkyl, $C_2$–$C_{18}$alkenyl, $C_5$–$C_8$cycloalkyl, $C_5$–$C_8$cycloalkenyl, phenyl, $C_7$–$C_9$phenylalkyl, —$CH_2$—S—$X_1$, —$(CH_2)_p$COO—$X_2$ or —$(CH_2)_q$O—$X_3$, the radicals $R_3$ are hydrogen, $R_4$ is hydrogen or $C_1$–$C_4$alkyl, $R_5$ is hydrogen, $C_1$–$C_4$alkyl, phenyl or CN, $R_6$ is hydrogen, $C_1$–$C_4$alkyl or phenyl, $R_7$ is hydrogen or $C_1$–$C_4$alkyl, $X_1$ is $C_1$–$C_{10}$alkyl, $C_5$–$C_8$cycloalkyl, phenyl, $C_7$–$C_9$-phenylalkyl or —$(CH_2)_r$COO—$Y_1$, $X_2$ is $C_1$–$C_{10}$alkyl, $C_5$–$C_8$cycloalkyl, phenyl or $C_7$–$C_9$-phenylalkyl, $X_3$ is $C_1$–$C_{10}$alkyl, $C_5$–$C_8$cycloalkyl, phenyl, $C_7$–$C_9$-phenylalkyl, $C_1$–$C_{10}$alkanoyl, $C_3$–$C_{18}$alkenoyl, $C_3$–$C_{18}$alkanoyl which is interrupted by oxygen; or benzoyl, and $Y_1$ is $C_1$–$C_{10}$alkyl, $C_5$–$C_8$cycloalkyl, phenyl or $C_7$–$C_9$phenylalkyl.

The radicals $R_8$, $R_9$, $R_{10}$, $R_{11}$, $R_{12}$, $R_{13}$ and $R_{14}$ are preferably hydrogen.

Also of interest is a compound of the formula I in which the radicals $R_1$, independently of one another, are $C_1$–$C_5$alkyl or $C_5$–$C_8$cycloalkyl, the radicals $R_2$, independently of one another, are $C_1$–$C_5$alkyl, the radicals $R_3$ are hydrogen, and $R_4$ is hydrogen or $C_1$–$C_4$alkyl.

Likewise of interest is a compound of the formula I in which the radicals $R_1$ are identical and are branched $C_3$–$C_5$alkyl, the radicals $R_2$ are identical and are $C_1$–$C_5$alkyl, the radicals $R_3$ are hydrogen, and $R_4$ is hydrogen or $C_1$–$C_4$alkyl.

Particular preference is given to a compound of the formula I in which

Y is oxygen or methylene,

Z is a

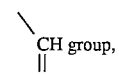

CH group, the radicals $R_1$ are identical and are branched $C_3$–$C_5$alkyl, the radicals $R_2$ are identical and are $C_1$–$C_5$alkyl, the radicals $R_3$ are hydrogen, $R_4$ is hydrogen or $C_1$–$C_4$alkyl, $R_5$ is hydrogen, $C_1$–$C_4$alkyl or CN, and $R_6$, $R_7$, $R_8$, $R_9$, $R_{10}$, $R_{11}$, $R_{12}$, $R_{13}$ and $R_{14}$ are hydrogen.

Of particular interest is the compound of the formula

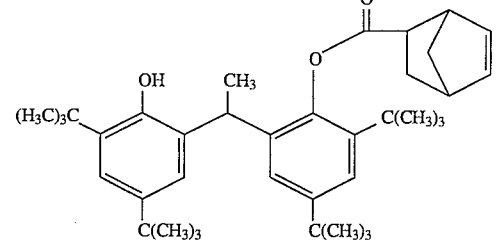

Z is preferably a

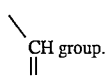
group.

Y is preferably oxygen or methylene.

The compounds of the formula I can be prepared, for example, by the following processes, which are known per se:

Process A

Reaction of a compound of the formula a

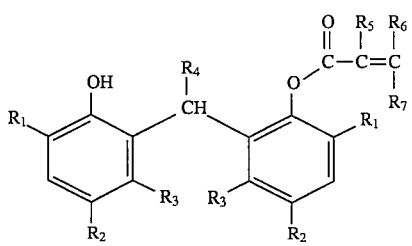

with a suitable compound of the formula b-1 or c (Diels-Alder reaction, as described, for example, in "Comprehensive Organic Synthesis, Vol. IV, 315 (1991), Pergamon Press, or Chem. Rev. 1993, 93,741–761"),

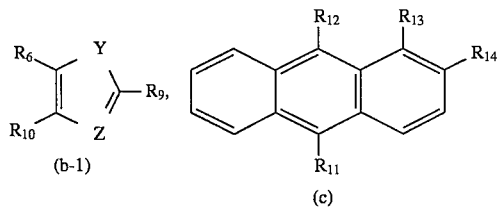

in which the variable radicals are as defined above.

This thermal Diels-Alder reaction can be carried out, for example, by mixing the two reactants in a suitable solvent at a temperature between room temperature and the boiling point of the reaction mixture. The reaction is preferably carried out in the absence of oxygen. Possible solvents are conventional hydrocarbons (for example toluene, hexane or cyclohexane), halogenated hydrocarbons (for example dichloromethane, dichloroethane or chlorobenzene), ethers (for example diethyl ether, tetrahydrofuran or dimethoxyethane), alcohols (for example methanol, ethanol or isopropanol), water or water/alcohol or water/ether mixtures.

If Y is methylene and Z is a

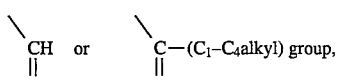

the compound of the formula b-1 can be replaced by a dimer of the formula b-2

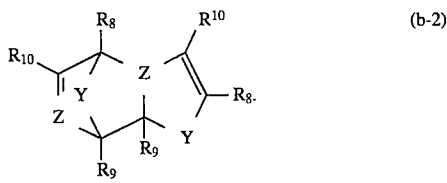

In this case, it is expedient to carry out the reaction at high temperatures, for example at 180°–220° C. (cracking temperature of a dimer such as dicyclopentadiene) in a closed system (autoclave) under pressure (for example 1–5 bar). The reaction can also be carried out without solvent.

The reaction can furthermore also be carried out at low temperatures (for example 0°–50° C.) in the presence of a Lewis acid as catalyst. The catalyst is preferably used in an amount of 2–50 mol %, in particular 2–10 mol %. Examples of suitable Lewis acids are R—Al—$Cl_2$ or $(R)_2$—AlCl, where R is methyl, ethyl, n-propyl or isopropyl, or furthermore $AlCl_3$, $SnCl_4$, $ZnCl_2$, $ZnJ_2$, $FeCl_3$ or $TiCl_4$.

Process B

Transesterification of carboxylic acid derivatives of the formula d or e

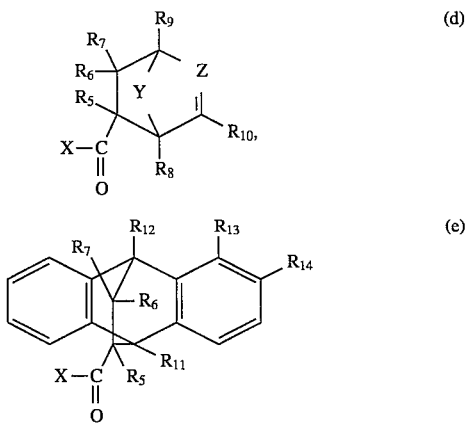

in which X is, for example, OH, Cl,

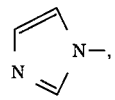

etc., using a bisphenol of the formula f,

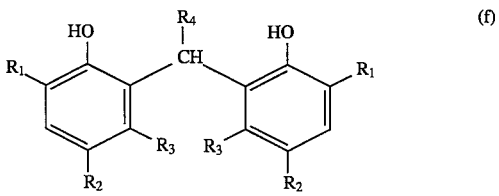

in which the variable radicals are as defined above.

The reaction can be carried out in a manner known per se, for example by adding one of the two starting materials to the second starting material and mixing the two reactants, preferably in the absence of oxygen. The reaction can be carried out with or without solvent (for example toluene). The temperature can be, for example, between the melting point and the boiling point of the reaction mixture, for example between −50° and 150° C., preferably between 0° and 150° C. The resultant product can likewise be purified by known methods, for example by evaporation of the solvent and crystallization of the crude product or by washing with water/HCl, extraction with an organic solvent, crystallization and/or chromatography. Preferred solvents for the extraction and for the chromatographic purification step are hexane, ethyl acetate or mixtures thereof.

If the carboxylic acid derivative of the formula d or e used in the reaction is an acid chloride (X═Cl), an acid acceptor can also be added to the reaction mixture. Examples of suitable acid acceptors are amines, such as pyridine or triethylamine. The amount of acid acceptor is preferably at least equivalent to the amount of the acid chloride. It is, for example, from 1 to 2 equivalents, in particular from 1.2 to 1.7 equivalents, based on the acid chloride.

The acid chloride can also be prepared in situ. In this case, the carboxylic acid of the formula d or e (X=OH), the bisphenol of the formula f and an acid acceptor (for example triethylamine) are introduced into a reactor, and phosphorus oxychloride is subsequently added analogously to the process described in, for example, U.S. Pat. No. 5,128,398.

It is furthermore also possible first to prepare the monosodium, monopotassium or monolithium phenoxide of the bisphenol of the formula f and then to react this with the acid chloride. The requisite phenoxides are prepared using hydrides, alkali metals, alkali metal hydroxides, alkali metal alkoxides or alkyllithium compounds as bases.

If the carboxylic acids of the formula d or e (X=OH) and the bisphenol of the formula f are employed directly as starting materials, the reaction is expediently carried out using reagents which take up liberated water, for example dicyclohexylcarbodiimide.

The starting materials used in the above-described process are known, some are commercially available, or they can be prepared analogously to known processes.

The compounds of the formula I are formed as isomer mixtures (endo-, exo-, cis- or trans-form, etc), which vary depending on the preparation process.

Examples of compounds of the formula I are shown in Table 1 below.

TABLE 1

| Compound | Structure | Elemental analysis Melting point |
|---|---|---|
| 101 | (structure with bisphenol bearing OH, two C(CH$_3$)$_3$ groups, CH bridge with CH$_3$, linked via O-C(=O) to norbornenyl group) | Elemental analyses and melting points are given in Examples 1 to 5. |
| 102 | (structure with bisphenol bearing OH, C(CH$_3$)$_3$, CH$_3$ substituents, CH$_2$ bridge, linked via O-C(=O) to norbornenyl group) | Elemental analysis<br>    C %   H %<br>Calc  80.83  8.75<br>Found  80.81  8.91<br>Melting point: 107–112° C. |
| 102 bis | (structure similar to 101 with additional CH$_3$ on norbornenyl group) | Elemental analysis<br>    C %   H %<br>calc.:  81.77  9.85<br>found:  81.71  9.94<br>Melting point: 73–81° C. |
| 103 | (structure with bisphenol bearing OH, two t-C$_5$H$_{11}$ groups, CH bridge with CH$_3$, linked via O-C(=O) to norbornenyl group) | Elemental analysis<br>    C %   H %<br>calc.:  82.03  10.16<br>found.:  82.17  10.23<br>Melting point: 118–121° C. |

TABLE 1-continued

| Compound | Structure | Elemental analysis Melting point |
|---|---|---|
| 104 | 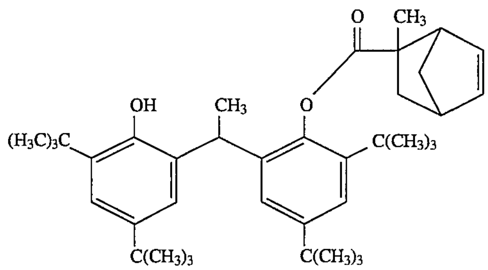 | Elemental analysis<br>　　　　C %　　H %<br>Calc　　81.77　　9.85<br>Found　　81.20　　9.99<br>Melting point: 132–140° C. |
| 105 | 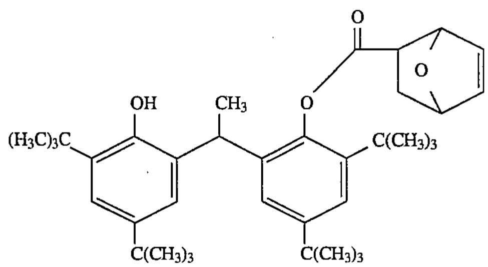 | Elemental analysis<br>　　　　C %　　H %<br>Calc.:　　79.24　　9.35<br>Found:　　78.78　　9.50<br>Melting point: 95–96° C. |
| 106 | 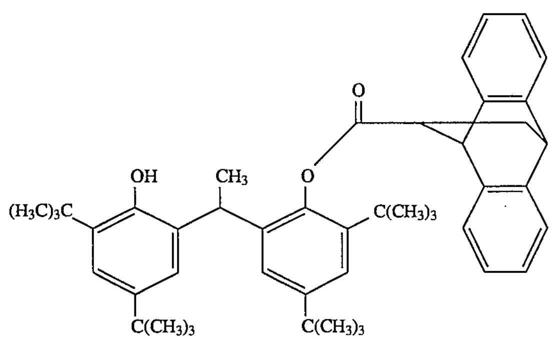 | Elemental analysis<br>　　　　C %　　H %<br>Calc　　84.13　　8.71<br>Found　　83.94　　8.85<br>Melting point: 217–219° C. |

The compounds of the formula I are suitable for stabilizing organic materials against thermal, oxidative or light-induced degradation. Examples of such materials are the following:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/ isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/ styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/ vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/ alkyl acrylate copolymers, acrylonitrile/alkoxyalkyl acrylate or acrylonitrile/vinyl halide copolymers or acrylonitrile/ alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamidcs staring from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA6.6 and copolymers, PA/HDPE, PA/PP, PA/PPO, PBT/PC/ABS or PBT/PET/PC.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The invention therefore furthermore relates to a composition comprising an organic material which is sensitive to oxidative, thermal or light-induced degradation and at least one compound of the formula I.

The organic material is preferably a synthetic polymer, in particular from the groups given above. Polyolefins and solution-polymerized polybutadiene rubber are particularly preferred. Likewise particularly preferred is solution-polymerized styrene-butadiene copolymer and styrene-butadiene block copolymer in which the ratio between styrene and conjugated butadiene is, for example, from 5:95 to 95:5. The proportion of polybutadiene in these copolymers is preferably from 5 to 30%.

In general, the compounds of the formula I are added to the organic material to be stabilized in amounts of from 0.01 to 10%, preferably from 0.01 to 5%, in particular from 0.05 to 0.5%, based on the total weight of the material to be stabilized.

The novel compounds can be incorporated into the organic material by known methods, for example before or during shaping or by applying the dissolved or dispersed compounds to the organic material, if necessary with subsequent evaporation of the solvent. The novel compounds can be added to the materials to be stabilized in the form of powders, granules or else in the form of a masterbatch which comprises these compounds for example in a concentration of from 2.5 to 25% by weight.

The compounds of the formula I can also be added before or during the polymerization or before the crosslinking, for example also during solution polymerization before evaporation of the solvent.

The materials stabilized in this way can be used in a wide variety of forms, for example as films, fibres, tapes, moulding compositions, profiles or as binders for surface coatings, adhesives or putties.

The stabilized organic materials of the invention may additionally also contain various conventional additives, such as, for example:

1. Antioxidants 1.1 Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methyl-undec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example $\alpha$-tocopherol, $\beta$-tocopherol, $\gamma$-tocopherol, $\delta$-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl) disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-($\alpha$-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidene(6-tert-butyl-4-isobutylphenol), 2,2'-methylenebis[6-($\alpha$-methylbenzyl)-4-nonylphenol], 2,2'-methylenebis[6-($\alpha$,$\alpha$-dimethylbenzyl)4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methy-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.7. O-, N- and S-benzyl compounds, for example 3,5,3',5'-tetra-tert-butyl-4,4'-dihydroxy-dibenzyl ether, octadecyl 4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxyphenylethyl)-isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β(3,5-di-tert-butyl-4-hydroxyphenyl)propionic acid with mono- or poly-hydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5,dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenypropionyl)hydrazine.

1.18. Ascorbic acid (vitamin C) 1.19. Aminic Antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)-diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylamino-phenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, Bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-di-hydro-3,3-dimethyl-4H-1,4-benzothiazine, phenothiazine, a mixture of mono- und dialkylated tert-butyl/tert-octylphenothiazines, a mixture of mono- und dialkylated tert-octylphenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$)$_3$—]$_2$, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-auroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl)n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tert-octyl-amino-2,6-dichloro-1,3,5-triazine, tris(2,2,6,6-tetramethyl-4-piperidinyl)nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine, and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-di-chloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid,2-undecyl-7,7,9,9-tetramethyl-1-oxa-3,8-diaza-4-oxospiro[4,5]decane, a reaction product of 7,7,9,9-tetramethyl-2-cycloundecyl-1-oxa-3,8-diaza-4-oxospiro [4,5]decane und epichlorohydrin.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazin 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1, 3,2-dioxaphosphocin, bis(2,4-di-tert-butyl-6-methylphenyl)methylphosphite, bis(2,4-di-tert-butyl-6-methylphenyl)ethylphosphite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexa-decyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridecyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-hepta-decyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers ("ionomers").

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4 316 611, DE-A-4 316 622, DE-A-4 316 876, EP-A-0 589 839 or EP-A-0 591 102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

The weight ratio between the novel compounds and the conventional additives can be, for example, from 1:0.5 to 1:5.

The invention furthermore relates to the use of the compounds of the formula I for stabilizing organic materials against oxidative, thermal or light-induced degradation.

The examples below illustrate the invention in greater detail. All amounts are by weight, unless stated otherwise.

EXAMPLE 1

Preparation of compound 101

A mixture of 1.5 g (3 mmol) of 2,2'-ethylidenebis[4,6-di-tert-butylphenol]monoacrylate (preparation, for example, analogously to EP-A-500 323) and 1.4 g (21 mmol) of cyclopentadiene in 40 ml of toluene is warmed to 90° C. and stirred at this temperature for two hours. The reaction mixture is subsequently evaporated in a vacuum rotary evaporator. Crystallization of the resultant crude product from acetonitrile gives 1.5 g (91% of theory) of compound 101 as a white powder (isomer mixture).

Melting point: 150°–154° C.

| Elemental analysis: | C % | H % |
| --- | --- | --- |
| calculated: | 81.67 | 9.74 |
| found: | 81.86 | 9.68 |

EXAMPLE 2

Preparation of compound 101

A mixture of 4.93 g (10 mmol) of 2,2'-ethylidenebis[4,6-di-tert-butylphenol]monoacrylate and 4.6 g (70 mmol) of cyclopentadiene in 20 ml of isopropanol and 20 ml of water is warmed to 90° C. and stirred at this temperature for two hours. The reaction mixture is subsequenfly evaporated in a rotary evaporator, and the residue is poured into water and extracted twice with ethyl acetate. The organic phases are combined, dried over sodium sulfate and evaporated in a vacuum rotary evaporator. Crystallization of the residue from acetonitrile gives 3.9 g (71% of theory) of compound 101 as a white powder (isomer mixture).

Melting point: 148°–150° C.

| Elemental analysis: | C % | H % |
| --- | --- | --- |
| calculated: | 81.67 | 9.74 |
| found: | 81.69 | 9.68 |

EXAMPLE 3

Preparation of compound 101

9.85 g (20 mmol) of 2,2'-ethylidenebis[4,6-di-tert-butylphenol]monoacrylate, 0.6 ml (1.08 mmol=5 mol %) of a 1.8M ethylaluminium dichloride solution in toluene and 50 ml of toluene are introduced into a 100 ml round-bottom flask under an $N_2$ atmosphere. 1.8 ml (22 mmol) of cyclopentadiene are added dropwise to this suspension at room temperature, and the mixture is stirred for 2½ hours. The orange solution obtained is subsequently poured into 50 ml of HCl (1M), and the mixture is extracted twice with ethyl acetate. The organic phases are combined, washed with an aqueous, saturated NaCl solution, dried over sodium sulfate and evaporated in a vacuum rotary evaporator. Crystallization of the residue (10.5 g) from acetonitrile gives 8.5 g (77% of theory) of compound 101 as a white powder (isomer mixture).

Melting point: 146°–150° C.

| Elemental analysis: | C % | H % |
|---|---|---|
| calculated: | 81.67 | 9.74 |
| found: | 81.70 | 9.87 |

EXAMPLE 4

Preparation of compound 101

49.3 g (0.1 mol) of 2,2'-ethylidenebis[4,6-di-tert-butylphenol]monoacrylate, 7.9 g (0.06 mol) of dicyclopentadiene and 50 ml of toluene are introduced into a 0.3 l autoclave. The autoclave is flushed with inert gas ($N_2$) and warmed at 200° C. for 8 hours (maximum pressure 3 bar). The yellow solution obtained is subsequently cooled to room temperature and evaporated in a vacuum rotary evaporator. Crystallization of the residue from acetonitrile gives 44.5 g (80% of theory) of compound 101 as a white powder (isomer mixture).

Melting point: 157°–160° C.

| Elemental analysis: | C % | H % |
|---|---|---|
| calculated: | 81.67 | 9.74 |
| found: | 81.81 | 9.85 |

EXAMPLE 5

Preparation of compound 101

A mixture of 4.4 g (10 mmol) of 2,2'-ethylidenebis[4,6-di-tert-butylphenol] and 2 g (13 mmol) of norborn-5-ene-2-carbonyl chloride (preparation, for example, analogous to J. Org. Chem. 38, 642 (1973)) is warmed to 140° C. and stirred at this temperature for 5 minutes, HCl being evolved from 125° C. The mixture is cooled to about 110° C., 15 ml of acetonitrile are added, and the mixture is cooled to room temperature. The product which crystallizes out is filtered off and dried in a high vacuum, giving 4.2 g (70% of theory) of compound 101 as a white powder (isomer mixture).

Melting point: 152°–155° C.

| Elemental analysis: | C % | H % |
|---|---|---|
| calculated: | 81.67 | 9.74 |
| found: | 81.65 | 9.96 |

Compounds 102 and 103 are prepared by the method described in Example 3 from methylenebis[4-methyl-6-tert-butylphenol]monoacrylate and 2,2'-ethylidenebis[4,6-di-tert-pentylphenol]monoacrylate respectively and cyclopentadiene.

Compound 102 bis is prepared analogously to the process described in Example 4 from methylcyclopentadiene dimer and 2,2'-ethylidenebis[4,6-di-tert-butylphenol]monoacrylate.

EXAMPLE 6

Preparation of compound 104

18 ml (29 mmol) of a 1.6N butyllithium/hexane solution are slowly added dropwise, under an $N_2$ atmosphere, to a solution, cooled to 5°–10° C., of 12.7 g (29 mmol) of 2,2'-ethylidenebis[4,6-di-tert-butylphenol] in 50 ml of tetrahydrofuran. The mixture is stirred for 15 minutes, and 6.5 g (38 mmol) of 2-methylnorborn-5-enecarbonyl chloride (prepared, for example, analogously to A. F. Jacobine et al.; J. of Appl. Polym. Sci. 45, 471 (1992)) in 6 ml of tetrahydrofuran are subsequently added dropwise. The mixture is refluxed overnight. After cooling to room temperature, the reaction mixture is filtered through Hyflo and evaporated in a vacuum rotary evaporator. Crystallization of the residue from acetonitrile gives 11.7 g (70% of theory) of compound 104 as a white powder (isomer mixture).

Melting point: 132°–140° C.

EXAMPLE 7

Preparation of compound 105

39.5 g (0.09 mmol) of 2,2'-ethylidenebis[4,6-di-tert-butylphenol] and 11.84 g (0.12 mmol) of triethylamine in 200 ml of toluene are introduced into a 500 ml round-bottom flask under an $N_2$ atmosphere. 16.5 g (0.1 mmol) of 7-oxabicyclo[2.2.1]hept-5-ene-2-carbonyl chloride (preparation, for example, analogous to Bull. Chem. Soc. Jpn., 57, 3339-40 (1984)) are added dropwise to this colourless solution at −20° C. The mixture is stirred at −20° C. for 30 minutes and then warmed to room temperature over the course of 2 hours. The salts are filtered off, and the filtrate is evaporated in a vacuum rotary evaporator. Chromatography of the residue on silica gel with the eluent hexane/ethyl acetate 80:1 gives 11.2 g (22% of theory) of compound 105 as a white powder (isomer mixture).

Melting point: 95°–96° C.

EXAMPLE 8

Preparation of compound 106

6.6 g (15 mmol) of 2,2'-ethylidenebis[4,6-di-tert-butylphenol] and 4.2 g (15.7 mmol) of 9,10-dihydro-9,10-ethanoanthracene-11-carbonyl chloride (preparation, for example, analogous to J.A.C.S. 94, 1193 (1972)) in 100 ml of toluene are introduced into a 250 ml round-bottom flask under an $N_2$ atmosphere. 2.7 ml (19.5 mmol) of triethylamine are added dropwise to this solution at about 5° C. The mixture is stirred at 5° C. for two hours, then poured into water and extracted twice with ethyl acetate. The organic phases are combined, washed with an aqueous, saturated sodium chloride solution, dried over sodium sulfate and evaporated in a vacuum rotary evaporator. Crystallization of the residue from methanol gives 6.6 g (62% of theory) of compound 106 as a pale-yellow powder (isomer mixture).

Melting point: 217°–219° C.

EXAMPLE 9

Stabilization of polypropylene during multiple extrusion 1.3 kg of polypropylene powder (®Profax 6501) which has been prestabilized with 0.025% of n-octadecyl 3-[3,5-di-tert-butyl-4-hydroxyphenyl]propionate and has a melt flow index of 3.2 at 230° C. and 2.16 kg are mixed with 0.05% of pentaerythrityl tetrakis[3-(3,5-di-tert-butyl-4-hydroxyphenyl)propionate], 0.05% of calcium stearate, 0.03% of dihydrotalcite [$Mg_{4.5}Al_2(OH)_{13}CO_3.3.5H_2O$] and 0.05% of a compound from Table 1. This mixture is extruded in an extruder having a barrel diameter of 20 mm and a length of 400 mm at 100 revolutions per minute, the 3 heating zones being set to the following temperatures: 260°, 270° and 280° C. The extrudate is cooled by drawing through a waterbath and is subsequently granulated. These granules are extruded a number of times. After 3 extrusions, the melt flow index is measured (at 230° C. and 2.16 kg). A large increase in the melt flow index denotes significant chain degradation, ie. poor stabilization. The results are shown in Table 2.

TABLE 2

| Compound from Table 1 | Melt flow index after 3 extrusions |
| --- | --- |
| — | 20.0 |
| 101 | 6.8 |
| 104 | 7.2 |

EXAMPLE 10

Stabilization of elastomers (Brabender test)

A styrene-butadiene-styrene elastomer (®Finaprene 902) is mixed with the stabilizer shown in Table 3 and compounded in a Brabender Plastograph at 200° C. and 60 revolutions/minute. The compounding resistance is recorded continuously as torque. As a consequence of crosslinking of the polymer, a rapid increase in torque occurs during the compounding time after initially remaining constant. The effectiveness of the stabilizers is evident from an extension of the time for which the torque remains constant. The values obtained are shown in Table 3.

TABLE 3

| 0.25% of stabilizer from Table 1 | Time in minutes before a torque increase |
| --- | --- |
| — | 24.2 |
| 101 | 53 |
| 104 | 62 |

EXAMPLE 11

Stabilization of styrene-butadiene block polymers

During thermal/oxidative damage to styrene-butadiene block polymers, crosslinking occurs in the rubber phase. This crosslinking results in an increase in the melt viscosity and therefore in the extrusion pressure during processing in an extruder or in an injection-moulding machine.

The processing stability of the styrene-butadiene block polymers is frequently tested in a capillary rheometer. In this test, the polymer melt is forced through a nozzle, in a similar manner to extrusion.

25 g of styrene-butadiene block polymer granules (®K-Resin KR-01 from ®Phillips Petroleum) containing 0.2% of n-octadecyl 3-[3',5'-di-tert-butyl-4'-hydroxyphenyl]propionate and 0.6% of tris[nonylphenyl]phosphite are dissolved in 250 ml of cyclohexane at room temperature.

The amount of stabilizer shown in Table 4 is dissolved in toluene and admixed with the polymer solution. The cyclohexane is subsequently evaporated off at 60° C. and 0.013 bar.

The resultant polymer is pressed at 180° C. to give sheets with a thickness of 2 mm, from which circular samples having a diameter of 8 mm are stamped. The samples are introduced into the sample channel of a ®Keyeness Galaxy V capillary rheometer and measured at 250° C. and a shear rate of 14.594 $sec^{-1}$. After a flow time of 6 minutes, the apparent shear rate is recorded for 30 minutes as a function of time. The gradient of this curve ($\Delta\eta/\Delta t$ in Pa sec/min) is a measure of the degree of crosslinking of the polymer and is therefore in direct correlation with the effect of the stabilizer. The smaller this value, the more effective the stabilizer.

The results are shown in Table 4.

TABLE 4

| 0.15% of stabilizer from Table 1 | $\dfrac{\Delta\eta\ (Pa\ sec)}{\Delta t\ (min)}$ |
| --- | --- |
| — | 23 |
| 101 | 5 |
| 102 | 7 |
| 103 | 4 |
| 104 | 2 |
| 105 | 4 |

What is claimed is:

1. A compound of the formula I

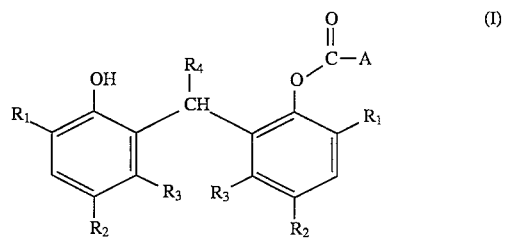

in which

A is a group of the formula IIa or IIb,

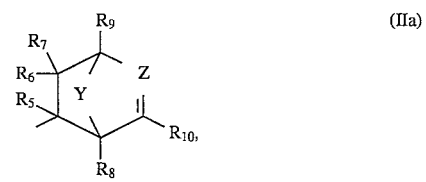

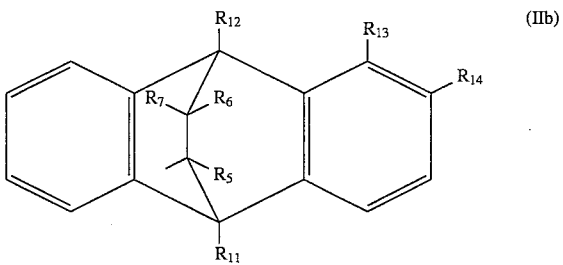

Y is oxygen, methylene, ethylidene or a >C=C(CH$_3$)$_2$ group,

Z is nitrogen,

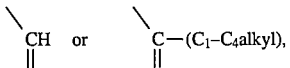

the radicals R$_1$, independently of one another, are C$_1$–C$_{25}$alkyl, C$_2$–C$_{24}$alkenyl, C$_5$–C$_{12}$cycloalkyl, C$_1$–C$_4$alkyl-substituted C$_5$–C$_{12}$cycloalkyl, C$_5$–C$_{12}$cycloalkenyl, C$_1$–C$_4$alkyl-substituted C$_5$–C$_{12}$cycloalkenyl, phenyl, C$_1$–C$_4$alkyl-substituted phenyl, C$_7$–C$_9$phenylalkyl or —CH$_2$—S—X$_1$, the radicals R$_2$, independently of one another, are hydrogen, C$_1$–C$_{25}$alkyl, C$_2$–C$_{24}$alkenyl, C$_5$–C$_{12}$cycloalkyl, C$_1$–C$_4$alkyl-substituted C$_5$–C$_{12}$cycloalkyl, C$_5$–C$_{12}$cycloalkenyl, C$_1$–C$_4$alkyl-substituted C$_5$–C$_{12}$cycloalkenyl, phenyl, C$_1$–C$_4$alkyl-substituted phenyl, C$_7$–C$_9$phenylalkyl, —CH$_2$—S—X$_1$, —(CH$_2$)$_p$COO—X$_2$ or —(CH$_2$)$_q$O—X$_3$, the radicals R$_3$, independently of one another, are hydrogen or C$_1$–C$_4$alkyl, R$_4$ is hydrogen or C$_1$–C$_8$alkyl, R$_5$ is hydrogen, C$_1$–C$_{10}$alkyl, phenyl, —CH$_2$—COO—X$_4$ or CN, R$_6$ is hydrogen, C$_1$–C$_4$alkyl, phenyl, —COO—X$_5$, —CN or —CON(X$_6$)(X$_7$), R$_7$ is hydrogen or C$_1$–C$_{10}$alkyl, R$_8$, R$_9$ and R$_{10}$, independently of one another, are hydrogen or C$_1$–C$_4$alkyl, R$_{11}$ and R$_{12}$, independently of one another, are hydrogen, C$_1$–C$_4$alkyl or phenyl, R$_{13}$ and R$_{14}$, independently of one another, are hydrogen or C$_1$–C$_4$alkyl, X$_1$ is C$_1$–C$_{25}$alkyl, C$_5$–C$_{12}$cycloalkyl, C$_1$–C$_4$alkyl-substituted C$_5$–C$_{12}$cycloalkyl, phenyl, C$_1$–C$_4$alkyl-substituted phenyl, C$_7$–C$_9$phenylalkyl or —(CH$_2$)$_r$COO—Y$_1$, X$_2$, X$_4$ and X$_5$, independently of one another, are C$_1$–C$_{25}$alkyl, C$_5$–C$_{12}$cycloalkyl, C$_1$–C$_4$alkyl-substituted C$_5$–C$_{12}$cycloalkyl, phenyl, C$_1$–C$_4$alkyl-substituted phenyl or C$_7$–C$_9$phenylalkyl, X$_3$ is C$_1$–C$_{25}$alkyl, C$_5$–C$_{12}$cycloalkyl, C$_1$–C$_4$alkyl-substituted C$_5$–C$_{12}$cycloalkyl, phenyl, C$_1$–C$_4$alkyl-substituted phenyl, C$_7$–C$_9$phenylalkyl, C$_1$–C$_{25}$alkanoyl, C$_3$–C$_{25}$alkenoyl, C$_3$–C$_{25}$alkanoyl which is interrupted by oxygen, sulfur or >N—Y$_2$, C$_6$–C$_9$cycloalkylcarbonyl, benzoyl, C$_1$–C$_4$alkyl-substituted benzoyl, thenoyl or furoyl, X$_6$ and X$_7$, independently of one another, are hydrogen, C$_1$–C$_{25}$alkyl, C$_2$–C$_{24}$alkenyl, C$_5$–C$_{12}$cycloalkyl, C$_1$–C$_4$alkyl-substituted C$_5$–C$_{12}$cycloalkyl, C$_5$–C$_{12}$cycloalkenyl, C$_1$–C$_4$alkyl-substituted C$_5$–C$_{12}$cycloalkenyl, phenyl, C$_1$–C$_4$alkyl-substituted phenyl or C$_7$–C$_9$phenylalkyl, Y$_1$ is C$_1$–C$_{25}$alkyl, C$_5$–C$_{12}$cycloalkyl, C$_1$–C$_4$alkyl-substituted C$_5$–C$_{12}$cycloalkyl, phenyl, C$_1$–C$_4$alkyl-substituted phenyl or C$_7$–C$_9$phenylalkyl, Y$_2$ is hydrogen or C$_1$–C$_8$alkyl, p is 0, 1 or 2, q is an integer from 0 to 8, and r is 1 or 2.

2. A compound according to claim 1, in which the radicals R$_1$, independently of one another, are C$_1$–C$_{18}$alkyl, C$_2$–C$_{18}$alkenyl, C$_5$–C$_8$cycloalkyl, C$_1$–C$_4$alkyl-substituted C$_5$–C$_8$cycloalkyl, C$_5$–C$_8$cycloalkenyl, C$_1$–C$_4$alkyl-substituted C$_5$–C$_8$cycloalkenyl, phenyl, C$_1$–C$_4$alkyl-substituted phenyl, C$_7$–C$_9$phenylalkyl or —CH$_2$—S—X$_1$, the radicals R$_2$, independently of one another, are hydrogen, C$_1$–C$_{18}$alkyl, C$_2$–C$_{18}$alkenyl, C$_5$–C$_8$cycloalkyl, C$_1$–C$_4$alkyl-substituted C$_5$–C$_8$cycloalkyl, C$_5$–C$_8$cycloalkenyl, C$_1$–C$_4$alkyl-substituted C$_5$–C$_8$cycloalkenyl, phenyl, C$_1$–C$_4$alkyl-substituted phenyl, C$_7$–C$_9$phenylalkyl, —CH$_2$—S—X$_1$, —(CH$_2$)$_p$COO—X$_2$ or —(CH$_2$)$_q$O—X$_3$, R$_5$ is hydrogen, C$_1$–C$_{10}$alkyl, phenyl or CN, R$_6$ is hydrogen, C$_1$–C$_4$alkyl or phenyl, X$_1$ is C$_1$–C$_{18}$alkyl, C$_5$–C$_8$cycloalkyl, C$_1$–C$_4$alkyl-substituted C$_5$–C$_8$cycloakyl, phenyl, C$_1$–C$_4$ alkyl-substituted phenyl, C$_7$–C$_9$phenylalkyl or —(CH$_2$)$_r$COO—Y$_1$, X$_2$ is C$_1$–C$_{18}$alkyl, C$_5$–C$_8$cycloalkyl, C$_1$–C$_4$alkyl-substituted C$_5$–C$_8$cycloalkyl, phenyl, C$_1$–C$_4$alkyl-substituted phenyl or C$_7$–C$_9$phenylalkyl, X$_3$ is C$_1$–C$_{18}$alkyl, C$_5$–C$_8$cycloalkyl, C$_1$–C$_4$alkyl-substituted C$_5$–C$_8$cycloalkyl, phenyl, C$_1$–C$_4$alkyl-substituted phenyl, C$_7$–C$_9$phenylalkyl, C$_1$–C$_{18}$alkanoyl, C$_3$–C$_{18}$alkenoyl, C$_3$–C$_{18}$alkanoyl which is interrupted by oxygen or >N—Y$_2$, C$_6$–C$_9$cycloalkylcarbonyl, benzoyl, C$_1$–C$_4$alkyl-substituted benzoyl, thenoyl or furoyl, and Y$_1$ is C$_1$–C$_{18}$alkyl, C$_5$–C$_8$cycloalkyl, C$_1$–C$_4$alkyl-substituted C$_5$–C$_8$cycloalkyl, phenyl, C$_1$–C$_4$alkyl-substituted phenyl or C$_7$–C$_9$phenylalkyl.

3. A compound according to claim 1, in which the radicals R$_1$, independently of one another, are C$_1$–C$_{10}$alkyl, C$_2$–C$_{18}$alkenyl, C$_5$–C$_8$cycloalkyl, C$_5$–C$_8$cycloalkenyl, phenyl, C$_7$–C$_9$phenylalkyl or —CH$_2$—S—X$_1$, the radicals R$_2$, independently of one another, are hydrogen, C$_1$–C$_{10}$alkyl, C$_2$–C$_{18}$alkenyl, C$_5$–C$_8$cycloalkyl, C$_5$–C$_8$cycloalkenyl, phenyl, C$_7$–C$_9$phenylalkyl, —CH$_2$—S—X$_3$, —(CH$_2$)$_p$COO—X$_2$ or —(CH$_2$)$_q$O—X$_3$, the radicals R$_3$ are hydrogen, R$_4$ is hydrogen or C$_1$–C$_4$alkyl, R$_5$ is hydrogen, C$_1$–C$_4$alkyl, phenyl or CN, R$_6$ is hydrogen, C$_1$–C$_4$alkyl or phenyl, R$_7$ is hydrogen or C$_1$–C$_4$alkyl, X$_1$ is C$_1$–C$_{10}$alkyl, C$_5$–C$_8$cycloalkyl, phenyl, C$_7$–C$_9$-phenylalkyl or —(CH$_2$)$_r$COO—Y$_1$, X$_2$ is C$_1$–C$_{10}$alkyl, C$_5$–C$_8$cycloalkyl, phenyl or C$_7$–C$_9$-phenylalkyl, X$_3$ is C$_1$–C$_{10}$alkyl, C$_5$–C$_8$cycloalkyl, phenyl, C$_7$–C$_9$-phenylalkyl, C$_1$–C$_{10}$alkanoyl, C$_3$–C$_{18}$alkenoyl, C$_3$–C$_{18}$alkanoyl which is interrupted by oxygen; or benzoyl, and Y$_1$ is C$_1$–C$_{10}$alkyl, C$_5$–C$_8$cycloalkyl, phenyl or C$_7$–C$_9$phenylalkyl.

4. A compound according to claim 1, in which R$_8$, R$_9$, R$_{10}$, R$_{11}$, R$_{12}$, R$_{13}$ and R$_{14}$ are hydrogen.

5. A compound according to claim 1, in which the radicals R$_1$, independently of one another, are C$_1$–C$_5$alkyl or C$_5$–C$_8$cycloalkyl, the radicals $R_2$, independently of one another, are $C_1$–$C_5$alkyl, the radicals $R_3$ are hydrogen, and $R_4$ is hydrogen or $C_1$–$C_4$alkyl.

6. A compound according to claim 1, in which the radicals $R_1$ are identical and are branched $C_3$–$C_5$alkyl, the radicals $R_2$ are identical and are $C_1$–$C_5$alkyl, the radicals $R_3$ are hydrogen, and $R_4$ is hydrogen or $C_1$–$C_4$alkyl.

7. A compound according to claim 1, in which

Y is oxygen or methylene,

Z is a

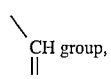

the radicals $R_1$ are identical and are branched $C_3$–$C_5$alkyl, the radicals $R_2$ are identical and are $C_1$–$C_5$alkyl, the radicals $R_3$ are hydrogen, $R_4$ is hydrogen or $C_1$–$C_4$alkyl, $R_5$ is hydrogen, $C_1$–$C_4$alkyl or CN, and $R_6$, $R_7$, $R_8$, $R_9$, $R_{10}$, $R_{11}$, $R_{12}$, $R_{13}$ and $R_{14}$ are hydrogen.

8. The compound

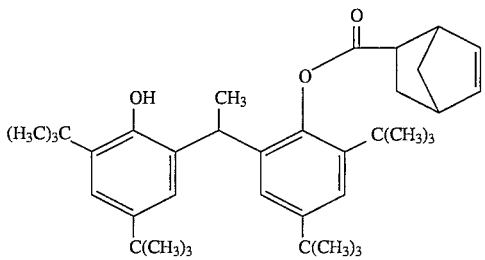

according to claim 1.

9. A composition comprising an organic material which is sensitive to oxidative, thermal or light-induced degradation and at least one compound of the formula I according to claim 1.

10. A composition according to claim 9, in which the organic material is a synthetic polymer.

11. A composition according to claim 9, in which the organic material is a polyolefin.

12. A composition according to claim 9, in which the organic material is a solution-polymerized polybutadiene rubber.

13. A composition according to claim 9, in which the organic material is a solution-polymerized styrene-butadiene copolymer or styrene-butadiene block copolymer.

14. A method for stabilizing an organic material against oxidative, thermal or light-induced degradation, which comprises incorporating in said organic material at least one compound according to claim 1.

* * * * *